United States Patent
Yeo et al.

(10) Patent No.: US 11,865,158 B2
(45) Date of Patent: Jan. 9, 2024

(54) PROCESS AND COMPOSITION MATTER OF NANOPARTICLE FORMULATION FOR SYSTEMIC TREATMENT OF SEPSIS

(71) Applicant: PURDUE RESEARCH FOUNDATION, West Lafayette, IN (US)

(72) Inventors: Yoon Yeo, West Lafayette, IN (US); Simseok Yuk, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 69 days.

(21) Appl. No.: 17/636,453

(22) PCT Filed: Aug. 21, 2020

(86) PCT No.: PCT/US2020/047289
§ 371 (c)(1),
(2) Date: Feb. 18, 2022

(87) PCT Pub. No.: WO2021/035102
PCT Pub. Date: Feb. 25, 2021

(65) Prior Publication Data
US 2022/0288162 A1   Sep. 15, 2022

Related U.S. Application Data

(60) Provisional application No. 62/890,304, filed on Aug. 22, 2019.

(51) Int. Cl.
| | |
|---|---|
| *A61K 38/17* | (2006.01) |
| *A61P 37/00* | (2006.01) |
| *A61K 9/51* | (2006.01) |
| *A61K 31/7032* | (2006.01) |
| *A61K 33/26* | (2006.01) |
| *A61K 38/12* | (2006.01) |
| *A61K 47/10* | (2017.01) |
| *A61K 47/36* | (2006.01) |

(52) U.S. Cl.
CPC ........ *A61K 38/1709* (2013.01); *A61K 9/5123* (2013.01); *A61K 31/7032* (2013.01); *A61K 33/26* (2013.01); *A61K 38/12* (2013.01); *A61K 47/10* (2013.01); *A61K 47/36* (2013.01); *A61P 37/00* (2018.01)

(58) Field of Classification Search
None
See application file for complete search history.

(56) References Cited

U.S. PATENT DOCUMENTS

| | | |
|---|---|---|
| 2011/0059162 A1 | 3/2011 | Reed et al. |
| 2013/0078210 A1 | 3/2013 | Yeo et al. |
| 2015/0196668 A1 | 7/2015 | Cheng et al. |
| 2017/0142967 A1 | 5/2017 | Reed et al. |
| 2017/0143755 A1 | 5/2017 | Yeo et al. |

FOREIGN PATENT DOCUMENTS

| | | |
|---|---|---|
| CN | 110547442 A | 12/2019 |
| WO | 2020198015 A1 | 10/2020 |

OTHER PUBLICATIONS

Eun Jung Cho, Kyung-Oh Doh, Jinho Park1, Hyesun Hyun, Erin M. Wilson, Paul W. Snyder, Michael D. Tsifansky & Yoon Yeo Zwitterionic chitosan for the systemic treatment of sepsis, Published: Jul. 14, 2016 Scientific Reports | 6:29739 | DOI: 10.1038/srep29739 (Year: 2016).*
Jordan A Kempker, Vin Tangpricha, Thomas R Ziegler and Greg S Martin, Title—Vitamin D in sepsis: from basic science to clinical impact Kempker et al. Critical Care 2012, 16:316 (Year: 2012).*
Hirotaka Ejima, Joseph J. Richardson, Kang Liang, James P. Best, Martin P. van Koeverden, Georgina K. Such, Jiwei Cui, Frank Caruso—One-Step Assembly of Coordination Complexes for Versatile Film and Particle Engineering—Jul. 12, 2013 vol. 341 Science www.sciencemag.org (Year: 2013).*
Shengqiu Chena, Yi Xiea, Tianjue Xiaoa, Weifeng Zhaoa,, Jianshu Lia, Changsheng Zhao—Tannic acid-inspiration and post-crosslinking of zwitterionic polymer as a universal approach towards antifouling surface, https://doi.org/10.1016/j.cej.2017.12.057 (Year: 2018).*
Sara A. Abouelmagda, Noura H. Abd Ellaha,f, Omar Amenb, Alshaimaa Abdelmoezc, Noha G. Mohamed—https://doi.org/10.1016/j.ijpharm.2019.03.009—Self-assembled tannic acid complexes for pH-responsive delivery of antibiotics: Role of drug-carrier interactions (Year: 2019).*
Gotts, J. E.; Matthay, M. A., Sepsis: pathophysiology and clinical management. BMJ 2016, 353, i1585.
Rudd, K. E. et al. Global, regional, and national sepsis incidence and mortality, 1990-2017: analysis for the Global Burden of Disease Study. The Lancet 395, 200-211 (2020).
Van der Poll, T., van de Veerdonk, F. L., Scicluna, B. P. & Netea, M. G. The immunopathology of sepsis and potential therapeutic targets. Nature Reviews Immunology 17, 407 (2017).
Beutler, B. & Rietschel, E. T. Innate immune sensing and its roots: the story of endotoxin. Nature Reviews Immunology 3, 169-176 (2003).

(Continued)

*Primary Examiner* — Robert A Wax
*Assistant Examiner* — Andre Mach
(74) *Attorney, Agent, or Firm* — Purdue Research Foundation

(57) ABSTRACT

The present invention generally relates to a process of nanoparticle formulations and its composition matter for systemic treatment of sepsis. In particular, this invention discloses a method for preparing tannic acid-ferric nanoparticles, optionally incorporating a component of vitamin $D_3$, coated with zwitterionic chitosan (ZWC) and polymyxin B (PMB). The invention described herein also pertains to pharmaceutical compositions and methods for the treatment of sepsis.

13 Claims, 8 Drawing Sheets

(56) References Cited

OTHER PUBLICATIONS

Rittirsch, D., Flierl, M. A. & Ward, P. A. Harmful molecular mechanisms in sepsis. Nature Reviews Immunology 8, 776-787 (2008).
Cavaillon, J.-M., Singer, M. & Skirecki, T. Sepsis therapies: learning from 30 years of failure of translational research to propose new leads. EMBO Mol Med 12, e10128 (2020).
Howell, M. D. & Davis, A. M. Management of Sepsis and Septic Shock. JAMA 317, 847-848 (2017).
Fink, M. P. & Warren, H. S. Strategies to improve drug development for sepsis. Nature Reviews Drug Discovery 13, 741 (2014).
Ranieri, V. M. et al. Drotrecogin Alfa (Activated) in Adults with Septic Shock. The New England Journal of Medicine 366, 2055-2064 (2012).
Sprung, C. L. et al. Hydrocortisone Therapy for Patients with Septic Shock. N Engl J Med 358, 111-124 (2008).
Opal, S. M. et al. Effect of Eritoran, an Antagonist of MD2-TLR4, on Mortality in Patients With Severe Sepsis: The Access Randomized Trial JAMA 309, 1154-1162 (2013).
López, A. et al. Multiple-center, randomized, placebo-controlled, double-blind study of the nitric oxide synthase inhibitor 546C88: Effect on survival in patients with septic shock*. 32, 21-30 (2004).
Reinhart, K. et al. Assessment of the safety and efficacy of the monoclonal anti-tumor necrosis factor antibody-fragment, MAK 195F, in patients with sepsis and septic shock: A multicenter, randomized, placebo-controlled, dose-ranging study. 24, 733-742 (1996).
Dellinger, R., Bagshaw, S. M., Antonelli, M. & et al. Effect of targeted polymyxin b hemoperfusion on 28-day mortality in patients with septic shock and elevated endotoxin level: The euphrates randomized clinical trial. JAMA 320, 1455-1463 (2018).
McCloskey, R. V., Straube, R. C., Sanders, C., Smith, S. M. & Smith, C. R. Treatment of septic shock with human monoclonal antibody HA-1A. A randomized, double-blind, placebo-controlled trial. Chess Trial Study Group. Annals of internal medicine 121, 1-5 (1994).
Marshall, J. C. Why have clinical trials in sepsis failed? Trends in Molecular Medicine 20, 195-203 (2014).
Buras, J. A., Holzmann, B. & Sitkovsky, M. Animal models of sepsis: Setting the stage. Nature Reviews Drug Discovery 4, 854-865 (2005).
Clinical and Laboratory Standards Institute, C. Methods for Dilution Antimicrobial Susceptibility Tests for Bacteria That Grow Aerobically; Approved Standard—9th Edition (Clinical and Laboratory Standards Institute, 2012).
Copeland, S., Warren, H. S., Lowry, S. F., Calvano, S. E. & Remick, D. Acute Inflammatory Response to Endotoxin in Mice and Humans. Clinical and Diagnostic Laboratory Immunology 12, 60 (2005).
Pranantyo et al., "Chitosan-Based Peptidopolysaccharides as Cationic Antimicrobial Agents and Antibacterial Coatings", Biomacromolecules Apr. 19, 2018, 19, 6, 2156-2165; Abstract; and figure 1.
Abouelmagd et al., "Tannic Acid-Mediated Surface Functionalization of Polymeric Nanoparticles", ACS Biomater. Sci. Eng. Dec. 12, 2016, 2, 12, 2294-2303; Abstract; materials and methods section.
Liu et al., "Zwitterionic Chitosan-Polyamidoamine Dendrimer Complex Nanoparticles as a pH-Sensitive Drug Carrier", Mol. Pharmaceutics Mar. 19, 2013, 10, 5, 1695-1704; Abstract; and entire document.
Smith et al., "Single-Step Self-Assembly and Physical Crosslinking of PEGylated Chitosan Nanoparticles by Tannic Acid", Polymers Apr. 27, 2019, 11(5), 749; Abstract.
International Search Report & Written Opinion of the International Search Authority for PCT/US20/47289 dated Nov. 23, 2020.
Krungchanuchat, S. et al., "Characterization and Cellular Studies of Molecular Nanoparticle of Iron (III)-Tannic Complexes; Toward a Low Cost Magnetic Resonance Imaging Agent," Biointerphases, vol. 12, Jun. 1, 2017.
Extended European Search Report issued by the European Patent Office, Munich, Germany, dated Aug. 14, 2023, for European Patent Application No. 20854838.8.

* cited by examiner

T = tannic acid-Fe nanoparticle;
D-T = vitamin $D_3$ tannic acid-Fe nanoparticle
PMB = polymyxin B
ZWC = zwitterionic chitosan
TZP = PMB bound nanoparticle

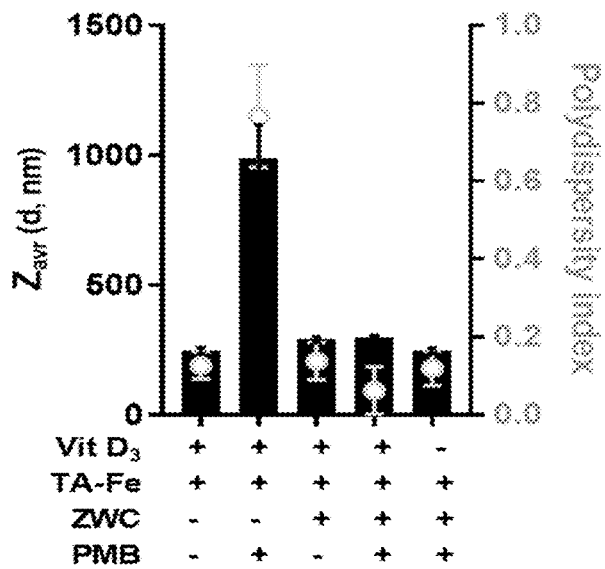
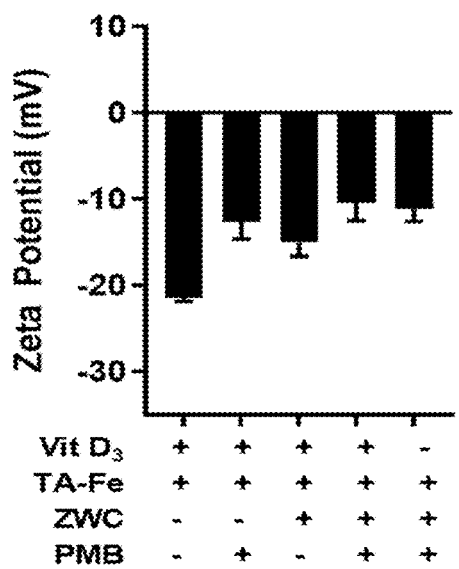
FIG. 2A
FIG. 2B
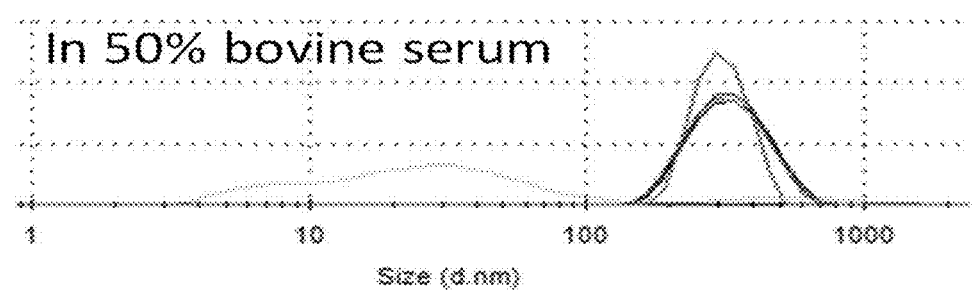
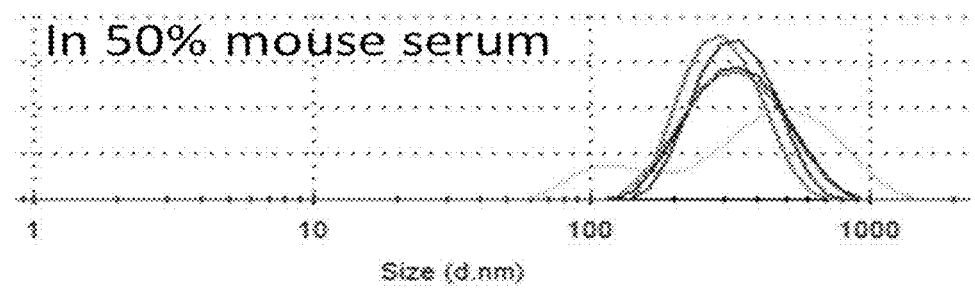
— 50% serum only  — After 15 h incubation in
— Fresh particles   — 50% serum (3 readings)
FIG. 2C

PROCESS AND COMPOSITION MATTER OF NANOPARTICLE FORMULATION FOR SYSTEMIC TREATMENT OF SEPSIS

CROSS-REFERENCE TO RELATED APPLICATIONS

This application is a 371 U.S. National Phase of PCT International Application No. PCT/US2020/047289 filed on Aug. 21, 2020, which claims benefit and priority to U.S. Provisional Application No. 62/890,304, filed on Aug. 22, 2019, the content of both are incorporated by reference herein in their entiries.

GOVERNMENT SUPPORT CLAUSE

This invention was made with government support under a grant AI119479, awarded by the National Institutes of Health. The government has certain rights in the invention.

TECHNICAL FIELD

The present invention generally relates to a process of nanoparticle formulations and its composition matter for systemic treatment of sepsis. In particular, this invention discloses a method for preparing tannic acid-Fe nanoparticles, optionally containing vitamin $D_3$, coated with zwitterionic chitosan (ZWC) and polymyxin B (PMB). The invention described herein also pertains to pharmaceutical compositions and methods for treating sepsis.

BACKGROUND

This section introduces aspects that may help facilitate a better understanding of the disclosure. Accordingly, these statements are to be read in this light and are not to be understood as admissions about what is or is not prior art.

Sepsis and septic shock are life-threatening conditions involving severe systemic inflammatory responses to infection. They are frequently encountered in the intensive care unit (ICU),[4] accounting for 4-17% of ICU admissions in high-income countries,[5] 17-26% of hospital mortality,[6] and $23.7 billion of hospital expenses.[7] In 2017, 48.9 million sepsis cases were reported worldwide, incurring 11 million deaths (19.7% of all global deaths) associated with sepsis.[2] Sepsis is caused by a massive invasion of bacterial and fungal pathogens, which introduce pathogen-associated molecular patterns (PAMPs) such as lipopolysaccharide (LPS) or lipoproteins into the system. The recognition of PAMPs by host immune systems induces the production and release of pro-inflammatory cytokines, chemokines, reactive oxygen species, and nitric oxide, mounting inflammatory responses to fight off the pathogens. In sepsis, the inflammatory responses continue without resolution, taking the host to a vicious cycle of hyperinflammation and compensatory immunosuppression. This leads to a high risk of additional infections and often fatal consequences such as disseminated intravascular coagulation (DIC) and multiple organ dysfunctions[3-6].

Currently, sepsis is treated by broad-spectrum antibiotics, fluid resuscitation, and vasopressors, aiming to manage early infections and support end-organ functions.[1] In addition to the standard care of sepsis, several experimental approaches have been undertaken over the years, resulting in more than 80 clinical trials since 1982.[8] These approaches have concerned various aspects of sepsis conditions, such as preventing DIC,[9] suppressing inflammation,[10] modulating immune responses,[11-13] and/or removing causative toxins or pathogens.[14,15] However, the existing strategies do not always improve patient outcomes, as evidenced by persistent sepsis mortality.[8,16] One of their limitations is that these approaches focus on modulating a specific pathway, which may be insufficient to address the multifaceted pathophysiology of sepsis.[1] High mortality rate and the lack of success in recent drug development efforts point to a critical unmet need for effective medical intervention. There are unmet needs for safer and more effective systemic treatments of sepsis.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 2A depicts particle size, polydispersity index of various compositions as shown.

FIG. 2B depicts zeta potential of various compositions as shown.

FIG. 2C depicts NP size stability in 50% bovine serum (top graph) or mouse serum (bottom graph) solutions.

DETAILED DESCRIPTION

Figure 1A:
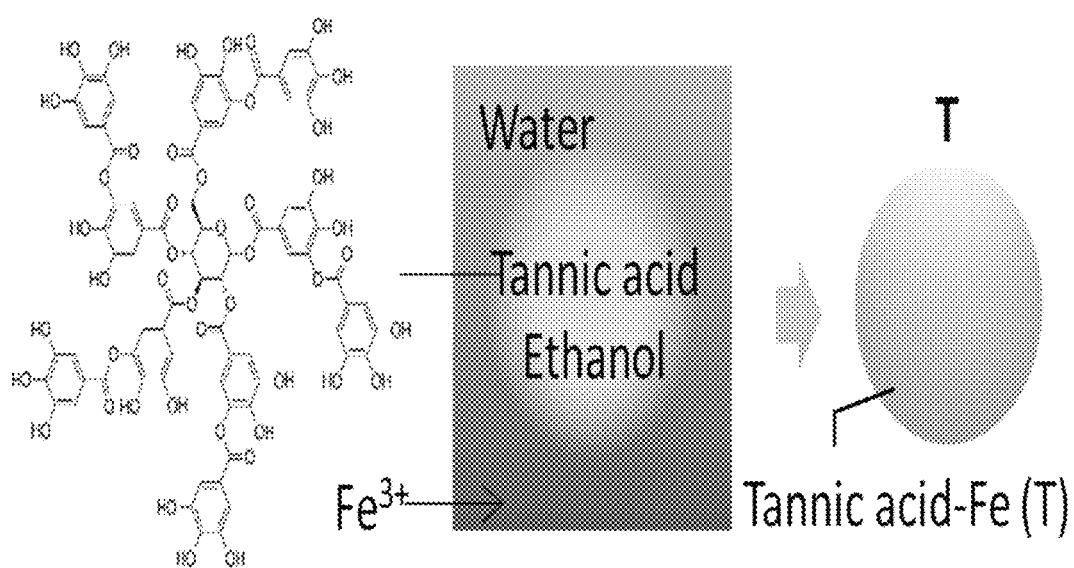
FIG. 1A shows schematic of tannic acid-Fe (T) core nanoparticles (NPs)

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

It is understood that a nanoparticle as disclosed herein is a tannic acid-Fe nanoparticle (T) coated with ZWC (Z) and PMB (P). Vitamin $D_3$ (D) are optionally encapsulated inside of the tannic acid-Fe nanoparticles. Therefore, the invention is TZP (tannic acid-Fe nanoparticles coated with ZWC and PMB) and D-TZP (TZP that contains vitamin $D_3$). PMB is loaded (i.e., coated) on, not inside said nano particle (NP), since PMB on the NP surface is meant to expose to the circulating blood and to make a contact with circulating LPS and pathogens to neutralize them. Vitamin $D_3$ is encapsulated inside of the NP and is released and metabolized in liver/kidneys.

The present invention generally relates to a process of nanoparticle formulations and its composition matter for systemic treatment of sepsis. In particular, this invention discloses a method for preparing tannic acid-ferric nanoparticles, optionally incorporating a component of vitamin $D_3$, coated with zwitterionic chitosan (ZWC) and polymyxin B (PMB). The invention described herein also pertains to pharmaceutical compositions and methods for the treatment of sepsis.

In some illustrative embodiments, this present disclosure relates to a process for preparing a pharmaceutical composition of zwitterionic chitosan (ZWC) coated-tannic acid-Fe (TZ) nanoparticles (NPs) comprising the step of:
a. adding an ethanol solution of tannic acid to an aqueous solution of $FeCl_3$ to afford tannic acid-Fe (T) nanoparticles (NPs);
b. preparing succinylated chitosan to afford zwitterionic chitosan (ZWC);
c. adding ZWC to said T NPs to afford ZWC-coated tannic acid-Fe NPs (ZWC-T NPs, or TZ); and
d. adding one or more active pharmaceutical ingredients at an elevated pH to above prepared TZ to afford a stable form of zwitterionic chitosan-coated tannic acid-Fe nanoparticles (TZ).

In some illustrative embodiments, this present disclosure relates to a process for preparing a pharmaceutical composition of zwitterionic chitosan (ZWC) coated-tannic acid-Fe (TZ) nanoparticles (NPs) as disclosed herein, wherein said ethanol solution of tannic acid further comprises a component of vitamin $D_3$.

In some illustrative embodiments, this present disclosure relates to a process for preparing a pharmaceutical composition of zwitterionic chitosan (ZWC) coated-tannic acid-Fe (TZ) nanoparticles (NPs) as disclosed herein, wherein said active pharmaceutical ingredient is a positively charged therapeutic compound.

In some illustrative embodiments, this present disclosure relates to a process for preparing a pharmaceutical composition of zwitterionic chitosan (ZWC) coated-tannic acid-Fe (TZ) nanoparticles (NPs) as disclosed herein, wherein said positively charged therapeutic compound is polymyxin B (PMB), polyethyleneimine, cathelicidin, colistin (aka polymyxin E), or an apolipoprotein.

In some illustrative embodiments, this present disclosure relates to a process for preparing a pharmaceutical composition of zwitterionic chitosan (ZWC) coated-tannic acid-Fe (TZ) nanoparticles (NPs) as disclosed herein, wherein said positively charged therapeutic compound is polymyxin B (PMB).

In some illustrative embodiments, this present disclosure relates to a product of a pharmaceutical composition of zwitterionic chitosan (ZWC) coated-tannic acid-Fe (TZ) nanoparticles (NPs) manufactured according to a process as disclosed herein.

In some illustrative embodiments, this present disclosure relates to a product of a pharmaceutical composition of zwitterionic chitosan (ZWC) coated-tannic acid-Fe (TZ) nanoparticles (NPs) manufactured according to a process as disclosed herein, together with one or more pharmaceutically acceptable diluents, excipients or carriers.

In some illustrative embodiments, this present disclosure relates to a product of a pharmaceutical composition of zwitterionic chitosan (ZWC) coated-tannic acid-Fe (TZ) nanoparticles (NPs) manufactured according to a process as disclosed herein, wherein said pharmaceutical composition is for the treatment of sepsis, together with one or more diluents, excipients or carriers, wherein said active pharmaceutical ingredient is polymyxin B (PMB).

In some illustrative embodiments, this present disclosure relates to a product of a pharmaceutical composition of zwitterionic chitosan (ZWC) coated-tannic acid-Fe (TZ) nanoparticles (NPs) manufactured according to a process comprising the steps of:
a. adding an ethanol solution of tannic acid to an aqueous solution of $FeCl_3$ to afford tannic acid-Fe (T) nanoparticles;

b. preparing succinylated chitosan to afford zwitterionic chitosan (ZWC);
c. adding ZWC to said tannic acid-Fe nanoparticles to afford zwitterionic chitosan coated tannic acid-Fe nanaoparticles (ZWC-T-NP, or TZ); and
d. adding one or more active pharmaceutical ingredients at an elevated pH to above prepared TZ to afford said pharmaceutical composition.

In some illustrative embodiments, this present disclosure relates to a product of a pharmaceutical composition of zwitterionic chitosan (ZWC) coated-tannic acid-Fe (TZ) nanoparticles (NPs) manufactured according to a process as disclosed herein, wherein said pharmaceutical composition further comprising one or more diluents, excipients or carriers.

In some illustrative embodiments, this present disclosure relates to a product of a pharmaceutical composition of zwitterionic chitosan (ZWC) coated-tannic acid-Fe (TZ) nanoparticles (NPs) manufactured according to a process as disclosed herein, wherein said ethanol solution of tannic acid further comprises a component of vitamin $D_3$.

In some illustrative embodiments, this present disclosure relates to a product of a pharmaceutical composition of zwitterionic chitosan (ZWC) coated-tannic acid-Fe (TZ) nanoparticles (NPs) manufactured according to a process as disclosed herein, wherein said active pharmaceutical ingredient is a positively charged therapeutic compound.

In some illustrative embodiments, this present disclosure relates to a product of a pharmaceutical composition of zwitterionic chitosan (ZWC) coated-tannic acid-Fe (TZ) nanoparticles (NPs) manufactured according to a process as disclosed herein, wherein said active pharmaceutical ingredient is polymyxin B.

In some illustrative embodiments, this present disclosure relates to a product of a pharmaceutical composition of zwitterionic chitosan (ZWC) coated-tannic acid-Fe (TZ) nanoparticles (NPs) manufactured according to a process as disclosed herein, wherein said active pharmaceutical ingredient is polymyxin B, polyethyleneimine, cathelicidin, colistin (aka polymyxin E), or an apolipoprotein.

In some illustrative embodiments, this present disclosure relates to a product of a pharmaceutical composition of zwitterionic chitosan (ZWC) coated-tannic acid-Fe (TZ) nanoparticles (NPs) manufactured according to a process as disclosed herein, wherein said product is for the systemic treatment of sepsis.

In some other illustrative embodiments, this present disclosure relates to a method for treating a patient of sepsis comprising the step of administering to the patient in need of relief from said sepsis a therapeutically effective amount of a pharmaceutical composition manufactured according to the following process:
a. adding an ethanol solution of tannic acid to an aqueous solution of $FeCl_3$ to afford tannic acid-Fe nanoparticles;
b. preparing succinylated chitosan to afford zwitterionic chitosan (ZWC);
c. adding ZWC to said tannic acid-Fe nanoparticles to afford zwitterionic chitosan coated tannic acid-Fe nanaoparticles (TZ);
d. adding one or more active pharmaceutical ingredients at an elevated pH to above prepared TZ; and
e. then adding one or more diluents, excipients or carriers to afford said pharmaceutical composition.

In some other illustrative embodiments, this present disclosure relates to a method for treating a patient of sepsis comprising the step of administering to the patient in need of relief from said sepsis a therapeutically effective amount of a pharmaceutical composition manufactured according to the process as disclosed herein, wherein said ethanol solution of tannic acid further comprises a component of vitamin $D_3$.

In some other illustrative embodiments, this present disclosure relates to a method for treating a patient of sepsis comprising the step of administering to the patient in need of relief from said sepsis a therapeutically effective amount of a pharmaceutical composition manufactured according to the process as disclosed herein, wherein said active pharmaceutical ingredient is a positively charged therapeutic compound.

In some other illustrative embodiments, this present disclosure relates to a method for treating a patient of sepsis comprising the step of administering to the patient in need of relief from said sepsis a therapeutically effective amount of a pharmaceutical composition manufactured according to the process as disclosed herein, wherein said positively charged therapeutic compound is polymyxin B, polyethyleneimine, cathelicidin, colistin (polymyxin E), or a apolipoprotein.

In some other illustrative embodiments, this present disclosure relates to a method for treating a patient of sepsis comprising the step of administering to the patient in need of relief from said sepsis a therapeutically effective amount of a pharmaceutical composition manufactured according to the process as disclosed herein, wherein said positively charged therapeutic compound is polymyxin B (PMB).

In some other illustrative embodiments, this present disclosure relates to use of a pharmaceutical composition in the preparation of a medicament for treating a disease, wherein said pharmaceutical composition is manufactured according to the process of:
a. adding an ethanol solution of tannic acid to an aqueous solution of $FeCl_3$ to afford tannic acid-Fe nanoparticles;
b. preparing succinylated chitosan to afford zwitterionic chitosan (ZWC);
c. adding ZWC to said tannic acid-Fe nanoparticles to afford zwitterionic chitosan coated tannic acid-Fe nanaoparticles (TZ);
d. adding one or more active pharmaceutical ingredients at an elevated pH to above prepared TZ; and
e. then adding one or more diluents, excipients or carriers to afford said pharmaceutical composition.

In some other illustrative embodiments, this present disclosure relates to use of a pharmaceutical composition in the preparation of a medicament for treating a disease, wherein said pharmaceutical composition is manufactured according to the process of as disclosed herein, wherein said ethanol solution of tannic acid further comprises a component of vitamin $D_3$.

In some other illustrative embodiments, this present disclosure relates to use of a pharmaceutical composition in the preparation of a medicament for treating a disease, wherein said pharmaceutical composition is manufactured according to the process of as disclosed herein, wherein said active pharmaceutical ingredient is a positively charged therapeutic compound.

In some other illustrative embodiments, this present disclosure relates to use of a pharmaceutical composition in the preparation of a medicament for treating a disease, wherein said pharmaceutical composition is manufactured according to the process of as disclosed herein, wherein said positively charged therapeutic compound is polymyxin B, polyethyleneimine, cathelicidin, colistin (polymyxin E), or a apolipoprotein.

In some other illustrative embodiments, this present disclosure relates to use of a pharmaceutical composition in the preparation of a medicament for treating a disease, wherein said pharmaceutical composition is manufactured according to the process of as disclosed herein, wherein said positively charged therapeutic compound is polymyxin B (PMB).

In some other illustrative embodiments, this present disclosure relates to use of a pharmaceutical composition in the preparation of a medicament for treating a disease, wherein said pharmaceutical composition is manufactured according to the process of as disclosed herein, wherein said disease is sepsis.

Objectives

The objective of this study is to develop a NP formulation with anti-LPS activity, comparable or superior to PMB in efficacy and potency but with no systemic toxicities, as well as immunomodulatory activity and to investigate its utility as a systemic therapy of sepsis.

Significant Results, Including Major Findings, Developments, or Key Outcomes

Figure 1B:
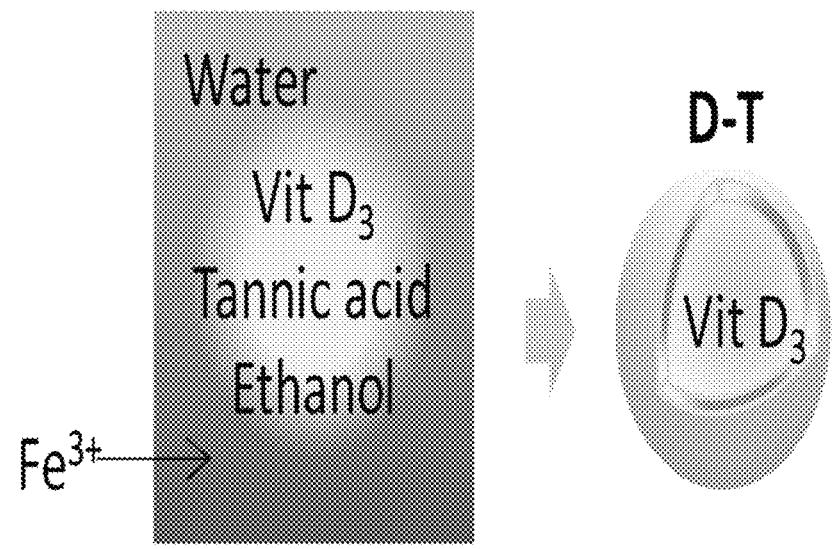
FIG. 1B shows schematic of tannic acid-Fe NPs containing vitamin $D_3$ core (D-T).
Figure 1C:
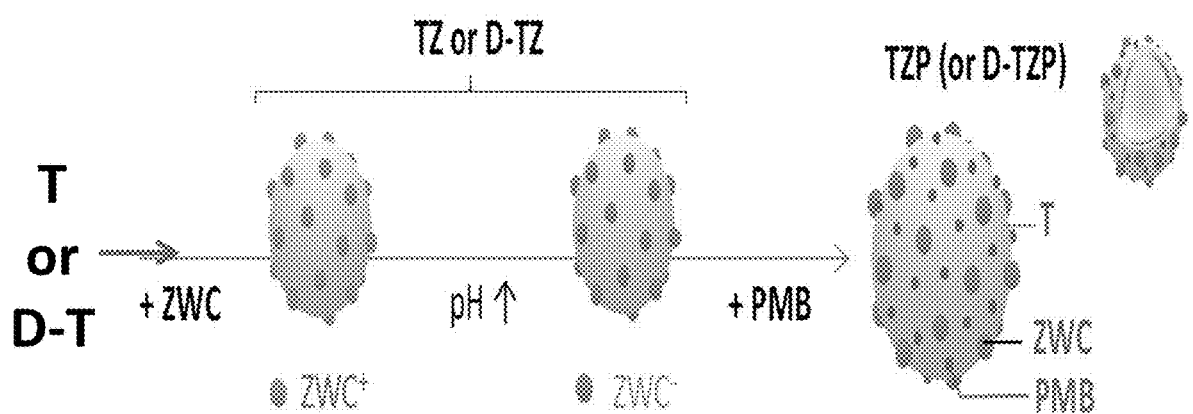
FIG. 1C shows schematic of variations of PMB-bound NPs (TZP or D-TZP).

Design and Production of Polymyxin B-Bound NPs (FIG. 1)

Design: PMB-bound NPs (TZP or D-TZP) are made of three components with distinct roles: (i) supramolecular tannic acid-Fe assemblies (T); (ii) succinylated chitosan (or zwitterionic chitosan; ZWC, Z); (iii) polymyxin B (PMB, P). The tannic acid-Fe assemblies serve as the NP platform and optionally encapsulates vitamin $D_3$ (D) as an anti-inflammatory agent. T NPs can incorporate thiol- or amine-terminated molecules via multiple mechanisms (Schiff base reaction, electrostatic interaction, hydrogen bonding, and hydrophobic interaction). Z and PMB are LPS adsorbents and bound on the NP surface via the reactivity of pT. Surface-bound, Z also prevents uncontrolled aggregation of NPs during the PMB loading.

Production: The NP platform (T or D-T) were produced in two forms. T particles were made by mixing ethanolic tannic acid with aqueous $FeCl_3$ solution (FIG. 1A), whereupon tannic acid and $Fe^{3+}$ form an instantaneous coordination complex. The nanocapsules containing vitamin $D_3$ (D-T) were produced by adding ethanolic solution of tannic acid and vitamin $D_3$ to aqueous $FeCl_3$ solution (FIG. 1B), which forms the tannic acid-$Fe^{3+}$ complex at the interface between ethanol and water making spherical nanocapsules containing vitamin $D_3$. ZWC and PMB were sequentially added to T or D-T to form PMB-bound NPs (TZP or D-TZP).

NP Characterization

Particle size & surface charge (FIG. 2): D-T particles had a z-average of 247 nm and zeta potential of −21 mV at pH 7.4. Without the surface-bound ZWC, D-T underwent uncontrolled aggregation upon the addition of PMB, reaching an average diameter of 986 nm. This is likely due to the high charge difference between PMB and D-T particles, which allow multiple particles to bridge via PMB. The surface-bound ZWC makes it less negatively charged (−15.0±1.6 mV of D-TZ vs. −21.4±0.5 mV of D-T) at pH 7.4; thus, while being able to attract PMB via electrostatic interaction, it reduced the avidity of interactions with PMB and prevented particle aggregation. The Z-averages of D-TZP and TZP were 297 and 247 nm, respectively.

Figures 2D, 2E, 2F:
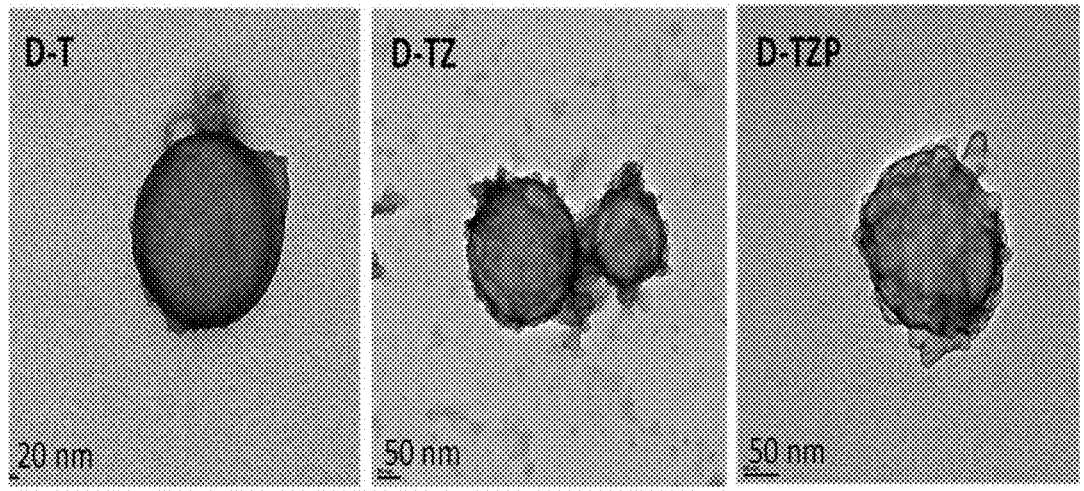
FIG. 2D depicts TEM images of D-T NPs.
FIG. 2E depicts TEM images of D-TZ NPs.
FIG. 2F depicts TEM images of D-TZP NPs.

Size stability: D-TZP maintained the size in 50% serum solution (bovine, murine) at 37° C. for 15 h, showing the potential to circulate with stable size. Morphology: Transmission electron microscopy revealed a spherical shape and rough tannic acid-$Fe^{3+}$ coat on D-TZ or D-TZP (FIG. 2d). Acetonitrile etching to remove vitamin $D_3$ core visualized the tannic acid-$Fe^{3+}$ layer (not shown). Drug loading: PMB and vitamin $D_3$ contents were 49.3±1.0 wt % (indirectly measured) and 23.0±0.7 wt %, respectively (n=3 independent batches).

D-TZP retains antibacterial activity of PMB. To test if D-TZP retains antibacterial activity of PMB, the minimum inhibitory concentrations (MICs) of the D-TZP and TZP, PMB, and control antibiotics (gentamicin and imipenem) were determined against four Gram-negative bacteria *Escherichia coli*, *Klebsiella pneumoniae* and *Pseudomonas aeruginosa* (Table 1). Both D-TZP and TZP showed antibacterial activity with 2-4 fold increase in MIC values compared to free PMB. At 2×MIC and 5×MIC, both D-TZP and PMB killed *Klebsiella pneumoniae* strain in 2 h. *Klebsiella pneumoniae* incubated with D-TZP or PMB at 5×MIC for 1.5 h was observed by SEM. Both D-TZP and PMB induced deformation of bacterial membrane, indicating that D-TZP killed the bacterial in the same mechanism as free PMB.

TABLE 1

Minimum inhibitory concentration (MIC) (μg/mL) of antibiotics, D-TZP, and control NPs.

| | *Escherichia coli* ATCC 2452 | *Escherichia coli* ATCC 2469 | *Klebsiella pneumoniae* NR-41920 | *Pseudomonas aeruginosa* NR-50573 |
|---|---|---|---|---|
| Gentamicin | >64 | >64 | 64 | 1 |
| Imipenem | 16 | 16 | 8 | 1 |
| D-T | >64 | >64 | >64 | >64 |
| D-TZ | >64 | >64 | >64 | >64 |
| D-TZP | 1 | 0.5 | 1 | 1 |
| TZP | 1 | 0.5 | 1 | 1 |
| PMB | 0.5 | 0.125 | 0.5 | 0.5 |

D-ZTP Binds to and Inactivates LPS: In Vitro

Figure 4A:
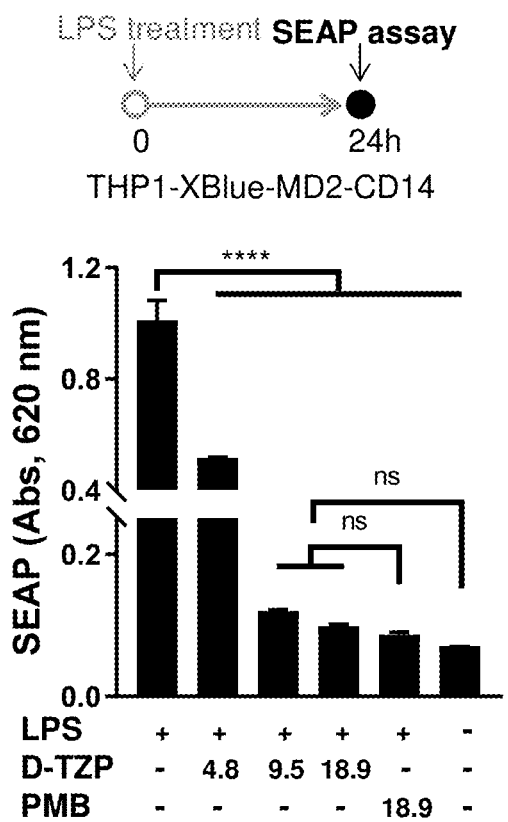
FIGS. 4A-4B shows SEAP assay of THP1-XBlue-MD2-CD14 cells incubated with LPS (FIG. 4A) added simultaneously with free PMB or D-TZP or (FIG. 4B) pretreated with them and separated from the complexes.
Figure 4B:
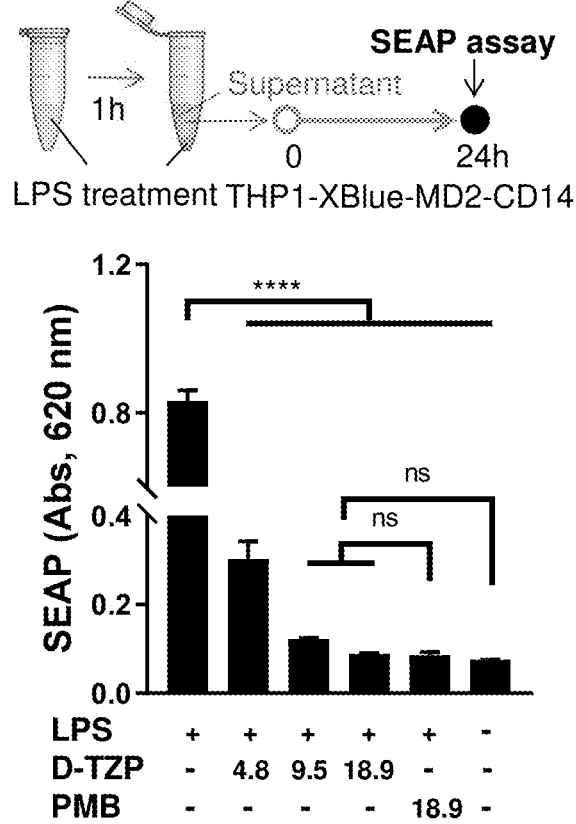

To investigate if D-TZP can neutralize LPS, a reporter cell line responding to LPS was incubated with LPS and free PMB or D-TZP's (with different amounts of PMB). THP1-XBlue-MD2-CD14, derived from the human monocytic THP-1 cell line, overexpresses MD2 and CD14 to amplify the response to TLR4 agonist LPS. Color change of the Quanti-Blue reagent (NF-kB/AP-1-inducible secreted embryonic alkaline phosphatase (SEAP) reporter protein) reflects NF-kB/AP-1 activation due to LPS. LPS-induced SEAP production was measured at 620 nm. The reporter cells with 10 ng/mL of LPS expressed a high level of SEAP as compared to non-challenged cells. Free PMB at 150 μg/mL as well as D-TZP eq. to 9.5-18.9 μg/mL PMB reduced the SEAP production, with no difference between free PMB and D-TZP at equivalent PMB concentration (FIG. 4A). This result indicates that D-TZP retained the LPS neutralizing effect of PMB. To determine how D-TZP reduced the SEAP production from the LPS-challenged reporter cells, 10 ng/mL of LPS was pretreated with PMB or D-TZP for 1 h, followed by centrifugation. A supernatant was obtained from each mixture to separate unbound LPS and added to THP1-XBlue-MD2-CD14 cells. The LPS pretreated with free PMB (equivalent to PMB 9.5-18.9 μg/mL) or D-TZP (equivalent to 18.9 μg/mL) induced significant reduction in SEAP production (FIG. 4B). This result indicates that the LPS/D-TZP interaction may account for the LPS neutralization.

NPs Reduce Toxicity of PMB

Figure 3A:
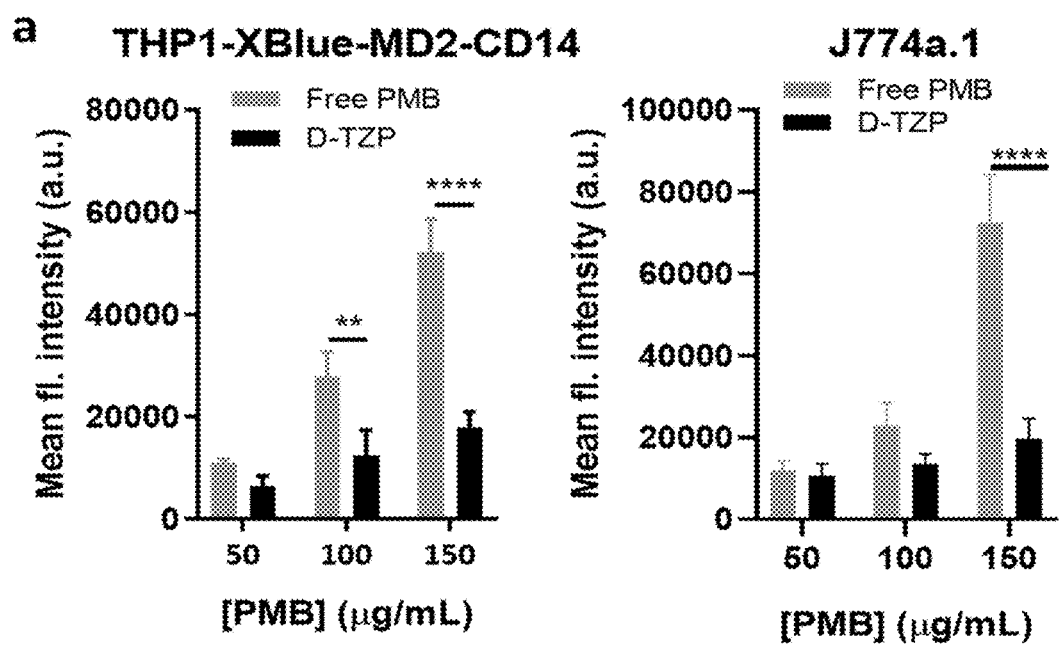
FIG. 3A shows mean fluorescence intensity of PI-stained THP1 monocytes (left side graph) or PI-stained J774a.1 macrophages (right side graph) after 24 h incubation with free PMB or D-TZP.
Figure 3B:
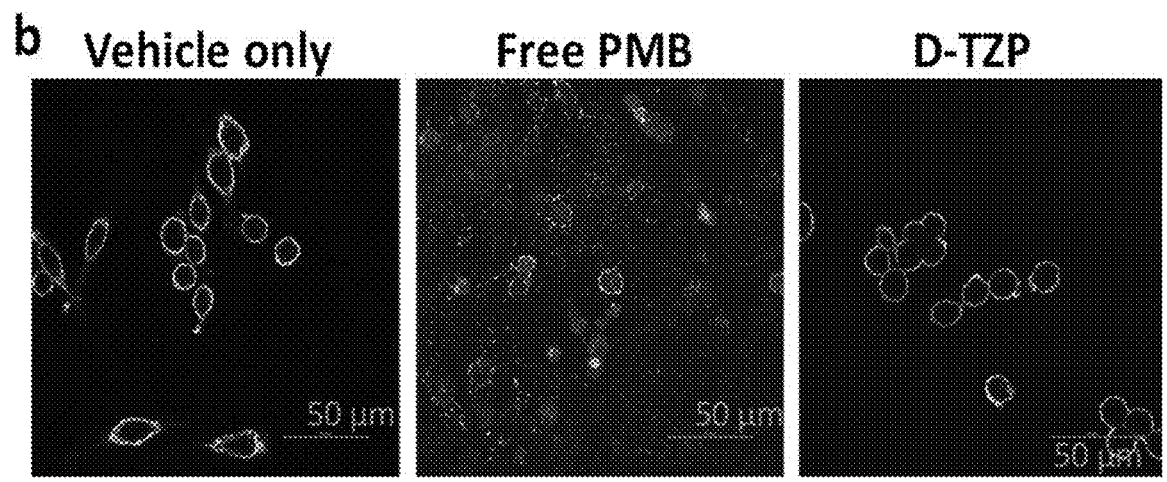
FIG. 3B shows confocal microscope images of J774a.1 macrophage membranes stained with wheat germ agglutinin (WGA, green) after treatment with vehicle (5% dextrose), free PMB (150 μg/mL), or D-TZP (eq. to 150 μg/mL PMB) for 12 h.
Figure 3C:
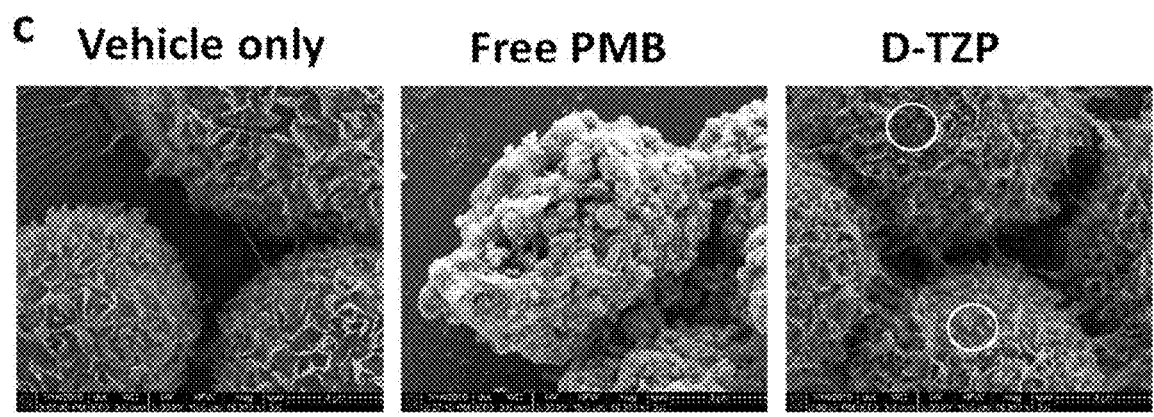
FIG. 3C shows SEM images of J774A.1 macrophages treated with vehicle (5% dextrose), free PMB (150 μg/mL), or D-TZP (eq. to 150 μg/mL PMB) for 12 h. The white circles in D-TZP treated cells indicate the areas the membrane-bound D-TZP particles are visible.

As a cationic polypeptide, PMB is known to be effective in neutralizing LPS as early as in 1967, but its systemic application is hampered by dose-limiting nephro- and neurotoxicity. PMB manifests the toxicity via the increased membrane permeability, resulting in increased influx of ions and water and subsequent cell swelling and lysis. To test if the toxicity can be reduced by supplying PMB as a NP-bound form, THP-1 monocytes or J774a.1 macrophages were incubated with D-TZP or free PMB at a concentration equivalent to 50-150 μg/mL PMB for 24 h, stained with propidium iodide (PI), which penetrates damaged cell membrane but not intact membrane, and analyzed with flow cytometry. The cells incubated with free PMB showed dose-dependent PI fluorescence signal (FIG. 3A), indicating the membrane damage due to PMB. In contrast, those treated with D-TZP showed much lower PI fluorescence than the equivalent dose of free PMB. Consistently, J774A.1 macrophages treated with D-TZP or free PMB showed differential cell membrane morphology. PMB caused significant membrane damage as shown by diffuse pattern of membrane staining with fluorescently labeled wheat germ agglutinin (FIG. 3B), whereas macrophages treated with D-TZP showed continuous membrane staining, comparable to the vehicle-treated cells. SEM images further support that D-TZP reduces the membrane toxicity of PMB substantially, as evident from the deformed membrane morphology of free PMB-treated cells vs. intact morphology of D-TZP-treated cells—despite the proximity to the cell surface (FIG. 3C). Substantial reduction of membrane damage is attributable to the surface-bound ZWC, which provides a negatively charged cloud beyond the remit of PMB due to the large size, attenuating direct exposure of PMB to cell membrane.

D-TZP was intraperitoneally (IP) or intravenously (IV) injected to C57BL/6 male mice at doses equivalent to as high as 40 mg/kg PMB and 10 mg/kg PMB, respectively, much greater than the known IP and IV $LD_{50}$ values of free PMB (20 mg/kg for IP and 5 mg/kg for IV). No mortality was observed, and weight loss was no more than 15% of their original weights. Higher doses have not been tested; therefore, the maximum tolerated dose of D-TZP in each route could not be defined. In contrast, free PMB exceeding its $LD_{50}$ resulted in mortality. The increased tolerated dose is consistent with the reduced in vitro toxicity of D-TZP.

D-TZP Reduces Mortality of Animals with LPS-Induced Sepsis

The therapeutic efficacy of D-TZP was tested in a mouse model of sepsis. C57BL/6 male mice were given IP injection of 20 mg/kg LPS, which causes systemic inflammation similar to initial clinical features of sepsis. TZP or D-TZP was administered in three regimens:

IP at 40 mg/kg PMB eq. simultaneously with LPS ([LPS+treatment], IP): All animals receiving D-TZP together with LPS survived (5/5) with the initial weight loss in 24 h and subsequent recovery in the next 3 days. In contrast, 1/5 of the control group receiving no treatment but vehicle (5% dextrose, D5W) survived and all others succumbed to death in 40 h from the challenge.

IP at 40 mg/kg PMB eq. immediately after LPS challenge (LPS, IP→treatment, IP): Given IP immediately after LPS challenge, D-TZP and TZP-treated group showed 100% survival (10/10 for D-TZP, 13/13 for TZP). None of the vehicle-treated control group survived (0/8).

Figures 5A, 5B:
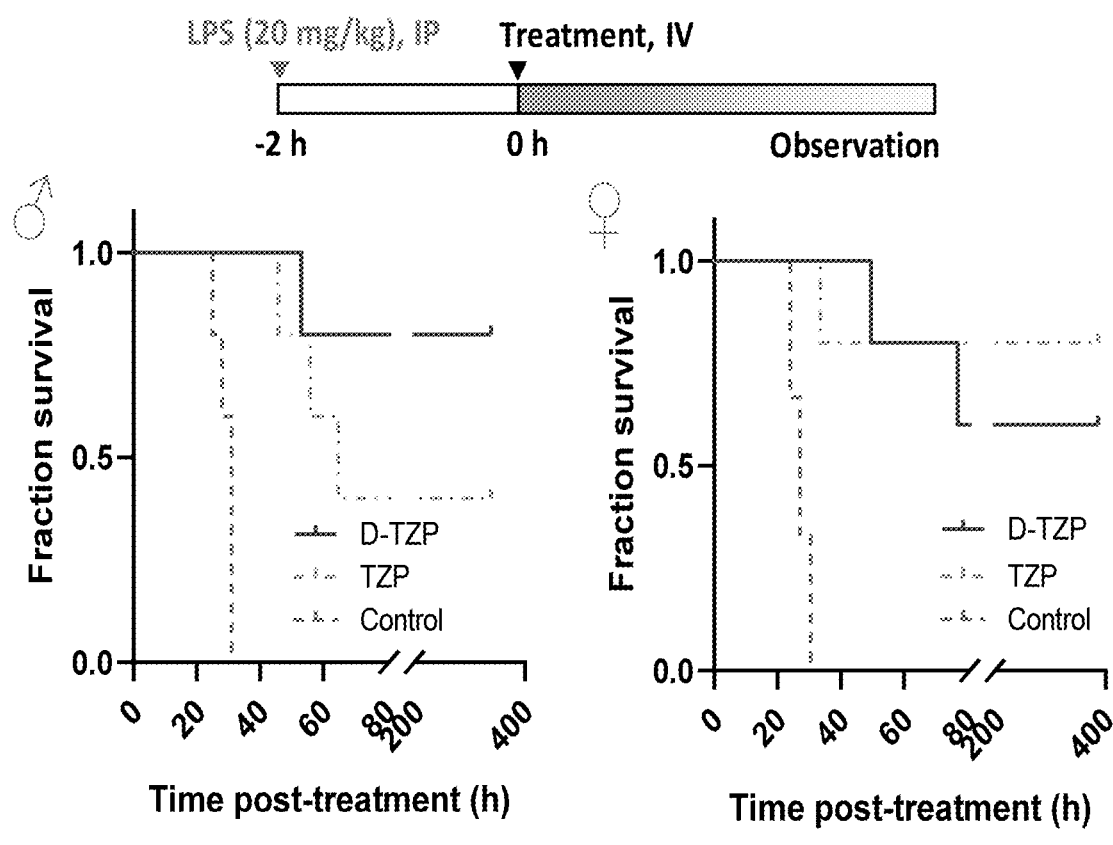
FIG. 5A shows survival fractions of C57BL/6 male mice challenged with LPS with or without PMB NPs treatment.
FIG. 5B shows survival fractions of C57BL/6 female mice challenged with LPS with or without PMB NPs treatment.

IV at 10 mg/kg PMB eq., 2 h post LPS-challenge (LPS, IP+2 h→treatment, IV) (FIGS. 5A-5B): Animals were challenged with IP LPS. After IP-injected LPS was systemically absorbed (2 h after the injection), D-TZP or TZP was injected IV. None of the vehicle-treated control (0/5 for male, 0/3 for female) survived, whereas those treated with D-TZP showed 60-80% survival (4/5 for male, 3/5 for female) and TZP 40-80% survival (2/5 for male, 4/5 for female).

D-TZP Reduces the Mortality of Mice with Cecal Ligation and Puncture.

Figure 6:
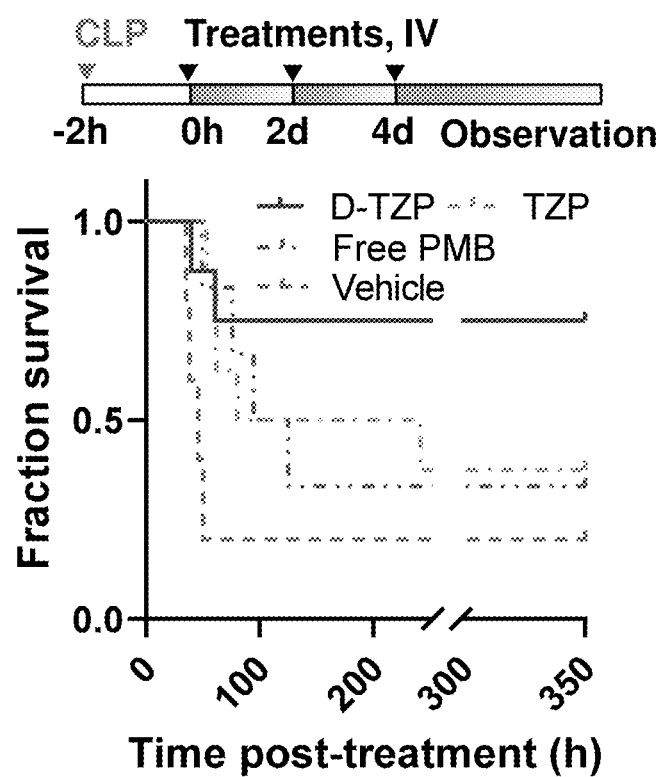
FIG. 6 shows the overall fractions of survival of C57BL/6 mice challenged with CLP and treated with PMB, TZP or D-TZP.

The efficacy of systemic D-LZP was further tested in cecal ligation and puncture (CLP) model, which induces systemic inflammation by polymicrobial infection and thus simulates a clinically relevant septic state (Toscano, M. G. et al., JoVE, e2860 (2011)). D-TZP and TZP was administered IV at 10 mg/kg PMB eq. 2 h post-CLP and every subsequent 2 days a maximum total of three times. Free PMB was given at 5 mg/kg IV in the same schedule as D-TZP. The animals receiving vehicle only had 20% survival (n=5), and those receiving free PMB showed a survival rate of 33% (n=6). Among the animals receiving D-TZP, 75% survived (n=8), recovering from hypothermia and initial weight loss. TZP saved 37.5% (n=8) with weight recovery (FIG. 6).

The protective effects of D-TZP are first attributable to PMB on the NP surface, which can capture LPS with high affinity and remove it from the system. This effect was achieved at concentrations that free PMB cannot be given. Of note, free PMB administered at the respective $LD_{50}$ (20 mg/kg for IP and 5 mg/kg for IV) did not protect the challenged animals and likely have aggravated the mortality due to the toxicity. D-TZP injected IP together with or immediately after IP LPS challenge may have formed complexes with LPS in the peritoneal cavity and prevented the systemic absorption of LPS. This may not be clinically relevant as sepsis is diagnosed after endotoxins are already in circulation. However, the therapeutic effect of D-TZP administered IV after systemic absorption of LPS is clinically significant as it indicates that D-TZP neutralizes circulating LPS and thus has the potential to attenuate the progression of established sepsis.

Additionally, given the difference between TZP and D-TZP in CLP model, vitamin $D_3$ appears to have a role in the survival of animals with polymicrobial sepsis induced by CLP. The active form of vitamin $D_3$, 1,25-dihydroxyviatmin D (1,25(OH)$_2$D), enhances the expression of cathelicidin, an endogenous broad-spectrum antimicrobial peptide[35] and LPS adsorbent[36], from the TLR-activated monocytes and macrophages as well as other leukocytes in humans. Moreover, 1,25(OH)$_2$D downregulates the synthesis of TLR2 and TLR4,[37] antagonizes the effect of LPS in proinflammatory cytokine production,[38] and downregulates tissue factors and upregulates thrombomodulin expression in monocytic cells to provide anticoagulation effects[39-41]. Therefore, the protective effects of D-TZP are also ascribed to the immunomodulatory effect of vitamin $D_3$.

Methods and Materials

Chemicals and reagents. Vitamin $D_3$ (meets USP testing specifications), tannic acid (ACS reagent), iron (III) chloride (reagent grade 97%), polymyxin B sulfate (meets USP testing specifications), colistin sulfate salt (≥15,000 U/mg), lipopolysaccharides (from *Escherichia coli* O111:B4), hydrogen peroxide 30 wt % solution in water (ACS reagent), hydrochloric acid (≥37%), succinic anhydride (≥99%), sodium phosphate dibasic molecular biology grade, sodium phosphate monobasic, and Tween 20 (viscous liquid) were purchased from Sigma-Aldrich (St. Louis, MO). Sodium hydroxide (Pellets) was purchased from Mallinckrodt. Chitosan (15 kDa; degree of deacetylation, 87%) was purchased from Polysciences, Inc. (Warrington, PA). Dialysis bag (a MW cut off 1000 Da) was purchased from Spectrum Laboratories (Rancho Dominguez, CA, USA). Trichloroacetic acid (5%, w/v) was purchased from RICCA Chemical Company (Arlington, TX). Sodium bicarbonate (Certified ACS), sodium sulfate (Certified ACS), acetic acid glacial (≥99.7%), acetonitrile (ACN, meets ACS specifications), Exel international disposable safelet I.V. catheters (20G), hexamethyldisilazane (HMDS), wheat germ agglutinin-Alexa fluor 488 conjugate, hoechst 33342, an antifade reagent (prolong gold antifade mountant), formalin (10%, w/v), paraformaldehyde 4% in 0.1 M phosphate buffer saline (pH 7.4), electron microscopy sciences formvar/carbon film 10 nm/1 nm thick on square 300 mesh copper grid, BD vacutainer plastic blood collection tubes with lithium heparin, 5-0 Perma-hand silk black braided suture, occuNomix™ hot rods warming pack, alcohol prep pad 200/PK, ethyl acetate (certified ACS), phosphate Buffered Saline Tablets (PBS) were purchased from ThermoFisher Scientific (Waltham, MA, USA). Flow cytometry staining buffer (1×) was purchased from R&D Systems (Minneapolis, MN, USA). Propidium iodide was purchased from VWR International (Radnor, PA). Ethanol (200 Proof, anhydrous, meets USP specs) was purchased from Decon Labs, Inc (King of Prussia, PA). 50% dextrose (injection, USP) was purchased from Hospira, Inc (Lake Forest, IL) and VetOne (Boise, ID). 18.2 MΩ/Deionized (DI) water was obtained from a Milli-Q ultrafiltration system (Millipore, Billerica, MA). Nair hair remover lotion was purchased from Church & Dwight Co., Inc (Ewing, NJ). Enzyme-linked immunosorbent assay (ELISA) kits for cytokines was purchased from BioLegend (San Diego, CA) and an ELISA kit for D-dimer was purchased from MyBioSource, Inc (San Diego, CA). Betadine 5% solution (sterile ophthalmic prep solution) was purchased from Alcon (Geneva, Switzerland). LubriFresh P.M. was purchased from Major Pharmaceuticals (Livonia, Michigan). Isoflurane, USP was purchased from Akorn (Lake Forest, Illinois).

Cell lines and reagents. THP1-XBlue-MD2-CD14 cell line, cell culture medium components, and secreted embryonic alkaline phosphatase (SEAP) reporter assay (QuantiBlue reagent), Normocin, Zeocin, and G418 were purchased from InvivoGen (San Diego, CA). Gibco Dulbecco's modified eagle's medium (DMEM, 4.5 g/L D-glucose, 584 mg/L L-glutamine, 110 mg/L sodium pyruvate), Gibco Roswell Park Memorial Institute 1640 medium (RPMI), Gibco Penicillin-Streptomycin (10,000 U/ml), and Gibco Dulbecco's Phosphate Buffered Saline (DPBS, without calcium chloride and magnesium chloride) were purchased from ThermoFisher Scientific (Waltham, MA, USA). Sodium pyruvate (100 mM, sterile filtered) and HEPES solution (1 M, pH 7.0-7.6, sterile-filtered) were purchased from Sigma Aldrich. Fetal bovine serum (FBS, premium) was purchased from Atlanta Biologicals (Flowery Branch, GA). J774A.1 macrophage cell line was purchased from ATCC (Manassas, VA).

Bacterial cell lines and reagents. *Escherichia coli* ATCC 2452 (NDM-1, isolated in Pakistan) was New Delhi metallo-beta-lactamase (NDM-1) positive, blaNDM positive by PCR, and carbepenem-resistant (Imipenem and Ertapenem). *Escherichia coli* ATCC 2469 (1001728, isolated from human urine) was New Delhi metallo-beta-lactamase (NDM-1) positive, blaKPC negative and blaNDM positive by PCR, and Carbepenem-resistant (Imipenem and Ertapenem). *Klebsiella pneumoniae* (NR-41920, isolated in 2008 from human blood culture in Boston, Massachusetts, USA) was Carbapenem-resistant strain, blaKPC-3 positive by PCR, and resistant to amikacin, ampicillin/sulbactam, cefazolin, cefepime, ceftazidime, ceftriaxone, cefuroxime, ciprofloxacin, gentamicin, meropenem, piperacillin/tazobactam, tobramicin and trimethoprim/sulfamethoxazole. *Pseudomonas aeruginosa* (NR-50573, isolated in early 1970s from the blood of a burn patient at Mercy Hospital in Pittsburgh, Pennsylvania, USA) was resistant to rifampicin and susceptible to meropenem, ofloxacin, ceftazidime, amikacin, and tobramycin. 0.5 McFarland standard was purchased from ThermoFisher scientific (Waltham, MA, USA). Mueller-Hinton broth and tryptone soy agar plates were purchased from Becton, Dickinson and company (Franklin Lakes, New Jersey, USA).

Animals. All animal procedures were approved by Purdue Animal Care and Use Committee, in compliance with the NIH guidelines for the care and use of laboratory animals. 6-8 week-old C57BL/6, BALB/c mice (male and female) were purchased Envigo (Indianapolis, IN, USA).

Synthesis and characterization of Low Molecular Weight Zwitterionic Chitosan (LMZWC). LMZWC was synthesized according to the previously reported method[59]. Five grams of chitosan was dissolved in 1% acetic acid (200 mL) and stirred for overnight. The solution was centrifuged at 4,000 rcf for 20 min. The supernatant was collected and freeze-dried to obtain an acetate salt form of chitosan. Three grams of chitosan acetate was dissolved in 200 mL of acidified water (pH 3, HCl) and stirred vigorously. For digestion, 30 mL of hydrogen peroxide (30 wt %) was added to the chitosan solution under vigorous stirring for 12 h. The digestion was quenched by the addition of 50 mL methanol, and the pH was adjusted to 7 by 1 N NaOH. The digested chitosan (low molecular weight chitosan, LMWC) was dialyzed against DI water with a molecular weight cut off (MWCO) of 1,000 Da for 2 days and freeze-dried. LMWC 400 mg was dissolved in 1% acetic acid (60 mL). The pH of the chitosan solution was titrated to 6 using 1 N $NaHCO_3$. Subsequently, 60 mg of succinic anhydride was added to achieve an anhydride to amine molar feed ratio (An/Am ratio) of 0.3. The pH of the mixture was maintained at 6 with 1 N $NaHCO_3$ for 30 minutes. The pH was then slowly increased to 8.5 with 1 N $NaHCO_3$ as the reaction proceeded. The reaction mixture was stirred overnight, followed by dialysis against DI water (pH adjusted to 8-9 by NaOH) with a MWCO of 1,000 Da. The purified LMZWC was freeze-dried and stored at −80° C. For routine quality control, the zeta potential of LMZWC was monitored varying the pH. LMZWC was dissolved to 1 mg/mL in 10 mM NaCl and titrated with 0.1 N HCl bringing the pH from 8 to 3. The zeta potential of LMZWC solution was measured by a Malvern Zetasizer Nano ZS-90 (Worcestershire, UK) at each addition of HCl.

Preparation of core nanoparticles. The core nanoparticles were produced in two forms. First, nanocapsules encapsulating vitamin $D_3$ (called D-T) were prepared by mixing ethanolic solution of vitamin $D_3$ and tannic acid and aqueous solution of $FeCl_3$ (FIG. 1B). Vitamin $D_3$ and tannic acid were dissolved in ethanol to 10 mg/mL and 40 mg/mL, respectively. $FeCl_3$ was dissolved in DI water to 10 mg/mL. The ethanolic vitamin $D_3$ solution (18 µL) was mixed with ethanolic tannic acid solution (10 µL). Aqueous $FeCl_3$ solution (10 µL) was added to 962 µL of DI water (4° C.). The diluted $FeCl_3$ solution was then added to the mixture of vitamin $D_3$ and tannic acid to initiate interfacial supramolecular assembly of tannic acid and $Fe^{3+}$ under probe sonication (Sonics Vibracell probe sonicator, Newtown, CT, USA) for 2 min, with 4 sec on, 2 sec off at 40% amplitude, forming D-T nanocapsules. The formation of tannic acid-$Fe^{3+}$ coordination complex was instantly evident from the characteristic blue color (Ejima, H. et al., *Science* 341, 154-157 (2013). Alternatively, nanoparticles omitting vitamin $D_3$ (called T) were prepared by mixing the ethanolic tannic acid with the aqueous $FeCl_3$ solution under probe sonication (FIG. 1A). The core nanoparticles (D-T or T)

were collected by centrifugation at 16,100 rcf for 20 min. Two batches were pooled and used for surface modification.

Surface modification of core nanoparticles. The core nanoparticles (D-T or T) collected from the previous step were incubated in LMZWC solution (4.5 mg in 1.5 mL DI water, acidified to pH 6.0) for 15 min. The pH was slowly raised to pH 8.5 using NaHCO$_3$ and incubated for additional 45 min. The LMZWC-coated nanoparticles (D-TZ or TZ) were collected by centrifugation at 16,100 rcf for 20 min. The LMZWC-coated nanoparticles were then incubated with polymyxin B (PMB, 800 µg in 1.5 mL DI water) for 1 h so that the cationic PMB was attracted to the particle surface via the negatively charged LMZWC. The PMB- and LMZWC-coated nanoparticles (D-TZP or TZP) were centrifuged at 16,100 rcf for 20 min, and the supernatant was analyzed by high-pressure liquid chromatography (HPLC). The particles were washed with DI water again and freeze-dried with 5% dextrose as a cryoprotectant. The freeze-dried particles were reconstituted in 5% dextrose. In the rest of this article, the PMB- and LMZWC-coated nanoparticles are referred to as D-TZP or TZP, depending on the inclusion of vitamin D$_3$ in the core.

Characterization of surface-modified nanoparticles. D-TZP and TZP were suspended in phosphate buffer (10 mM, pH 7.4), and their sizes and zeta potentials were measured by a Malvern Zetasizer Nano ZS90. Nanoparticle morphology was observed by Tecnai transmission electron microscopy (FEI, Hillsboro, OR, USA) after negative staining with 1% uranyl acetate. To visualize the PMB and LMZWC-bound tannic acid/iron coating, D-TZP was incubated in a 100% ethanol for 1 h, collected by centrifugation at 16,100 rcf for 20 min, and imaged by TEM. To confirm covalent conjugation of ZWC on D-T, D-T and D-TZ were analyzed by Fourier-transform infrared (FT-IR) spectroscopy. D-T were dissolved in DI water. LMZWC and D-TZ were dissolved in DI water after adjusting the pH to 6.0 and 8.5, respectively. All formulations were lyophilized and analyzed by the Thermo Nicolet Nexus 470 FT-IR (Madison, WI, USA).

Vitamin D$_3$ content. D-TZP was precisely weighed and dissolved in ethanol for 1 h to extract vitamin D$_3$. Vitamin D$_3$ in the supernatant was collected by centrifugation and quantified by the Agilent 1100 HPLC system equipped with Ascentis C18 column (25 cm×4.6 mm, particle size: 5 µm). The sample injection volume was 50 µL. The mobile phase was a 75:25 volume mixture of methanol and ACN and ran at 1 mL/min. The column temperature was maintained at 40° C. Vitamin D$_3$ was detected by a UV detector at a wavelength of 265 nm. Vitamin D$_3$ was dissolved in ethanol to 50-400 µg/mL and analyzed in the same condition to establish a calibration curve. The vitamin D$_3$ content in D-TZP was calculated as the vitamin D$_3$ amount divided by the D-TZP mass.

Polymyxin B sulfate (PMB) content. The PMB content in TZP or D-TZP was indirectly determined by measuring the unbound PMB remaining in the supernatant after 1 h incubation of PMB with TZ or D-TZ. Briefly, 0.8 ml of supernatant was collected and mixed with 0.2 mL of acetonitrile (ACN). HPLC analysis was conducted with an Agilent 1100 HPLC system (Palo Alto, CA, USA) equipped with Ascentis C18 column (25 cm×4.6 mm, particle size: 5 µm). The sample injection volume was 20 µL. The mobile phase was a 76:24 volume mixture of aqueous Na$_2$SO$_4$ solution (30 mM, pH 2.5) and ACN and eluted at a flow rate of 1 mL/min. The column temperature was maintained at 35° C. PMB was detected at a wavelength of 215 nm. PMB were dissolved in the mobile phase to 50-400 µg/mL and analyzed in the same condition to build a calibration curve. The surface-conjugated PMB was calculated by subtracting the unbound PMB from the PMB feed. The PMB content was calculated as the PMB amount divided by the nanoparticle mass.

In vitro PMB and Vitamin D$_3$ release in 50% FBS. D-TZP equivalent to 80 µg of PMB was suspended in 0.6 mL of 50% FBS and incubated at 37° C. under constant rotation. At regular time points, the suspension was centrifuged at 16,100 rcf for 20 min. The supernatant was sampled for analysis and replaced with fresh 50% FBS. At each sampling and medium replacement, the nanoparticles were briefly probe-sonicated and returned to the previous incubation condition. After the final sampling, the pellets were disintegrated in a mixture of 0.1 mL of 2 N HCl, 0.3 mL of DI water, and 0.1 mL of ACN, briefly probe-sonicated and analyzed by HPLC after filtration. Vitamin D$_3$ and PMB in the sampled supernatant were analyzed by HPLC and LC-MS/MS, respectively.

HPLC analysis of vitamin D. The supernatant was mixed with 1.4 mL of ethyl acetate and vigorously shaken for 1 h. The organic phase was separated by centrifugation at 16,100 rcf for 20 min and dried in a desiccator. The dry mass containing vitamin D$_3$ was dissolved in 0.2 mL ethanol and analyzed by HPLC. The pellets were disintegrated in a mixture of 0.16 mL of DI and 0.84 mL of ethanol, briefly probe-sonicated and analyzed by HPLC.

LC-MS/MS analysis of PMB. The sampled release medium was mixed with 5 µL of colistin sulfate (CS, 1 mg/mL, DI water) as an internal standard. To precipitate serum proteins, 0.6 mL of trichloroacetic acid was added to the mixture and vigorously shaken for 1 h. PMB was separated by centrifugation at 16,100 rcf for 20 min. ACN 0.3 mL and 8 µL of pyridine were added to the supernatant and analyzed by LC-MS/MS (Agilent 6460 QQQ with the Agilent 1200 Rapid Resolution HPLC). Atlantis dC18 column (15 cm×2.1 mm, particle size: 3 µm) was used for the analysis. Agilent 6460 QQQ equipped with Agilent Jet Stream Electrospray Ionization was operated in the positive ion. The following parameters were used for operation: dwell time: 200 ms; collision energy: 15 V; cell accelerator voltage: 7 V; and fragmentor: 160 V. The precursor ions (M/Z) for PMB and CS were 602.3, and 585.3, respectively. The product ions (M/Z) for PMB and CS were 241.1. The injection volume was 10 µL. A gradient chromatography was performed with 0.1% formic acid in DI water (A) and 0.1% formic acid in ACN (B) at a flow rate of 0.3 ml/min. Initially, the column started with the mobile phase consisting of 90% solvent A and 10% solvent B, and a linear gradient was then applied, decreasing solvent A from 90% to 5% over 10 min. Subsequently, solvent A was returned to 90% in 1 min. The mobile phase was maintained as the initial condition to re-equilibrate for additional 5 min. PMB was dissolved in DI water to 0.39-25 µg/mL and analyzed in a similar manner to build a calibration curve.

Nanoparticle stability in serum. To evaluate the size stability, D-TZP equivalent to 25 to 100 µg PMB were suspended in 1 mL of 50% FBS and incubated for 24 h at 37° C. The particle size distribution was measured by a Malvern Zetasizer Nano Z590.

Cell culture. THP1-XBlue-MD2-CD14 cells, derived from the human monocytic THP-1 cell line, were cultured in RPMI 1640, supplemented with 10% FBS, 1% penicillin/streptomycin, 1 mM sodium pyruvate, 10 mM HEPES, 100 µg/mL Normocin, 200 µg/mL Zeocin, and 250 µg/mL G418. J774A.1 macrophages were cultured in DMEM, supplemented with 10% FBS and 1% penicillin/streptomycin.

In vitro anti-LPS activity. Five microliters of LPS (100 ng/mL) was mixed with 15 µL of free PMB, D-TZP, or TZP at different concentrations in a flat-bottom 96-well plate. THP1-XBlue-MD2-CD14 cell suspension ($10^5$ cells in 180 µL) was then added to the mixtures. After 24 h incubation, cells were centrifuged at 233 rcf for 5 min. Twenty microliters of the cell medium was mixed with the Quanti-Blue reagent. After 2 h incubation, the color was measured at 620 nm by a Spectra Max M3 microplate reader (Molecular Devices, Sunnyvale, CA). In another test, 5 µL of LPS was pre-incubated with 15 µL of free PMB, D-TZP, or TZP for 1 h. Each mixture was centrifuged at 16,100 rcf for 20 minutes to separate a supernatant. The supernatant (20 µL) was incubated with THP1-XBlue-MD2-CD14 cell suspension ($10^5$ cells in 180 µL) for 24 h. The medium was analyzed in the same manner as above.

Cytotoxicity of PMB and D-TZP. Cytotoxic concentration range of free PMB was first determined with THP1-XBlue-MD2-CD14 cells by the MTT assay. The cells were seeded in a 96 well plate at a density of $10^5$ cells per well, and treated with PMB ranging from 25 µg/mL to 150 µg/mL. After 24 h incubation, the medium was removed by centrifugation (233 rcf, 5 min), and the cells were resuspended in 115 µL of medium containing 86 µg of MTT and incubated for 3.5 h. 100 µL of stop solution was added, and the plate was incubated in 37° C. for 24 h to dissolve the crystal. Next, cytotoxicity of PMB and D-TZP was compared using propidium iodide (PI) and flow cytometry. THP1-XBlue-MD2-CD14 cells were seeded in a 24-well plate at a density of $5\times10^4$ cells per well with 462.5 µL of complete medium. After overnight incubation at 37° C. in a 5% $CO_2$ atmosphere, the cells were treated with free PMB or D-TZP. After 24 h of incubation, the cells were collected by centrifugation at 233 rcf for 5 min. The cell pellet was dispersed in 300 µL of flow cytometry staining buffer. Twelve microliters of PI (10 µg/mL) was added to cells, and the mixture was incubated in the dark for 1 min. The PI fluorescence of 10,000 cells was measured with the BD Accuri C6 flow cytometer (BD Biosciences, San Jose, CA) via the FL-2 detector. Nanoparticles and cell debris were excluded by gating, but all cell population (dead or alive) was analyzed. J774A.1 macrophages were plated in a 12-well plate at a density of $1\times10^5$ cells per well with 0.925 mL of complete medium and treated in the same manner.

Effect of PMB and D-TZP on cell membrane. The effect of D-TZP on J774A.1 cell membrane was monitored by two methods (scanning electron microscopy and confocal microscopy). For scanning electron microscopy, J774A.1 macrophages were plated in a 6-well plate at a density of $3\times10^5$ cells per well with 3 mL of complete medium. After overnight incubation at 37° C. in a 5% $CO_2$ atmosphere, the cells were treated with either free PMB or D-TZP at a concentration equivalent to 150 µg/mL PMB for 12 h. The cells were centrifuged at 233 relative centrifugal force (rcf) for 3 min. The medium was removed, and 2.5% glutaraldehyde solution was added for fixation overnight at 4° C. The cells were then rinsed three times with water (5 min each) and incubated in 2% Osmium tetroxide for 1 h. After rinsing another three times with water (5 min each), the cells were dehydrated with a series of ethanol gradients (50%, 75%, 95%) for 10 minutes at each step. The dehydrated cells were rinsed with 100% ethanol three times for 10 minutes each time, stored in a 1:1 mixture of HMDS and ethanol in 1:1 for 30 min, and rinsed with 100% HMDS for 30 min twice. After overnight drying, the cells were placed on a carbon tape attached to an aluminum stud and coated with platinum for SEM analysis. The morphology of treated J774a.1 cells then was observed by a FEI NOVA NanoSEM scanning electron microscope (SEM). For confocal microscopy, J774A.1 macrophages were plated in a 12-well plate at a density of $10^5$ cells per well with 0.925 mL of complete medium. The cells were treated in the same way as above, collected by centrifugation at 233 rcf for 3 min, and fixed with 4% paraformaldehyde in PBS for 15 min. The fixed cells were stained with wheat germ agglutinin (5 µg/mL) for 10 min and Hoechst 33342 (1 µM) for 5 min, mounted on a glass slide with an antifade reagent (Prolong Gold Antifade Mountant), and imaged with a Nikon A1Rsi confocal microscope.

Hemolysis assay. Blood was obtained from 8 week-old BALB/c mice (male) by cardiac puncture and collected in a BD Vacutainer tube (lithium heparin). Red blood cells (RBC) were isolated by 10 min centrifugation at 1,000 rcf and rinsed with 210 mM NaCl solution until the supernatant was no longer red (three times). The rinsed RBC were incubated at 37° C. for 1 h with free PMB or D-TZP in 5% dextrose, at concentrations equivalent to PMB 50-150 µg/mL. Five percent dextrose and Tween 20 (0.1 mM) were used as negative and positive control, respectively. After 1 h incubation, the RBC suspension was centrifuged at 1,000 rcf for 5 min to separate a supernatant. The absorbance of the supernatant was measured at 541 nm by the SpectraMax M3 microplate reader.

Antimicrobial activities The minimum inhibitory concentrations (MICs) of the control antibiotics (gentamicin and imipenem), PMB, D-TZP and TZP against *Escherichia coli*, *Klebsiella pneumoniae* and *Pseudomonas aeruginosa* strains were determined by the broth microdilution method, according to guidelines outlined by the Clinical and Laboratory Standards Institute (CLSI)[18]. The bacterial stains were grown aerobically overnight on tryptone soy agar plates at 37° C. Afterwards, a bacterial solution equivalent to 0.5 McFarland standard was prepared and diluted in cation-adjusted Mueller-Hinton broth (CAMHB) to achieve a bacterial concentration of ~$5\times10^5$ CFU/mL. The treatments were added in the first row of the 96-well plates and serially diluted with media containing bacteria. Plates were incubated aerobically at 37° C. for 16-18 hours. MICs are reported as the minimum concentration of the treatments that completely inhibited the visual growth of bacteria.

Effect on bacterial membrane. *Klebsiella pneumoniae* NR-41920 was treated with either vehicle (5% dextrose), free PMB or D-TZP at 5×MIC for 1.5 h. The bacteria were collected by centrifugation at 5000 rcf for 10 min, fixed in 2.5% glutaraldehyde solution at 4° C., and placed on poly-1-lysine coated coverslip. After 1 h, the coverslip was rinsed three times with water (5 min each) and incubated in 2% Osmium tetroxide for 30 min. SEM imaging was performed as described in previous section.

In vivo safety. 6-10 week-old C57BL/6 male mice were used to evaluate the safety of D-TZP and TZP in comparison with free PMB. The treatment was administered by IP (2.5-40 mg/kg) or IV (3-10 mg/kg) injection. The body weight changes were monitored daily up to 1 week. For blood chemistry and histology analysis, blood and major organs were collected at 12 h post IV injection of vehicle (5% dextrose), free PMB, D-TZP, or TZP (all equivalent to 10 mg/kg PMB). Animals were sacrificed by $CO_2$ asphyxiation. Blood was obtained by cardiac puncture. Major organs were fixed in 10% formalin, embedded in paraffin, sectioned, and stained with hematoxylin and eosin for histological evaluation. The samples were imaged with a Nikon 90i upright microscope. To evaluate the safety of multiple intravenous injections, 5 mg/kg PMB or 10 mg/kg PMB equivalent D-TZP was given every 2 days up to 4 times total with body weight monitoring over 2 weeks.

Therapeutic efficacy in LPS-induced endotoxemia model. 6-8 week-old C57BL/6 mice (male and female) were challenged with an intraperitoneal injection of 20 mg/kg LPS solution (5% dextrose) via 20G catheter (Exel International Disposable Safelet I.V.), which causes systemic inflammation similar to initial clinical features of sepsis[17,19]. D-TZP or TZP was administered in three regimens: (i) IP at 40 mg/kg PMB eq. simultaneously with LPS ([LPS+treatment], IP); (ii) IP at 40 mg/kg PMB eq. immediately after LPS challenge (LPS, IP→treatment, IP); and (iii) IV at 10 mg/kg PMB eq., 2 h post LPS-challenge (LPS, IP+2 h→treatment, IV). A vehicle control (5% dextrose) or an equivalent dose of free PMB were given in the same manner for comparison. The PMB dose used in these studies are higher than its reported $LD_{50}$ for each route (20 mg/kg for IP, 5 mg/kg for IV). Buprenorphine (0.05 mg/kg) was injected subcutaneously shortly after the treatment and every 2-12 h as the signs of discomfort were observed. The body temperature was measured with a Pocket Infrared Thermometer (Braintree Scientific, Inc., Braintree, MA) at each observation, and the body weight was recorded at each observation. When an animal was found dead at the time of observation, the time of death was estimated to be in the halfway of the last two observation times. When animals were lethargic and cold at the time of observation, the animals were euthanized by $CO_2$ asphyxiation. The mouse survival was monitored for 2 weeks.

Therapeutic efficacy in polymicrobial sepsis model by cecal ligation and puncture (CLP). The efficacy of D-TZP and TZP was evaluated in a cecal ligation and puncture (CLP) model, the gold standard of polymicrobial sepsis model. The abdomen of 6 week-old C57BL/6 male was cleaned with a hair-removal cream (Nair, Church & Dwight Co., Inc). The mice were anesthetized by 2.5% isofluorane. Betadine 0.5% solution and 70% isopropyl alcohol swap were alternately applied three times to disinfect the shaved abdomen. Midline laparotomy was performed under an aseptic condition to exteriorize the cecum. The cecum was ligated below the ileocecal valve with a 5-0 suture (permahand silk, Ethicon) and perforated twice with 20 G needle on the same side of the cecum to release feces into the peritoneal cavity. After perforation, the intestines were returned to abdominal cavity. The abdominal wall and the skin were closed sutured with 5-0 suture. Buprenorphine (0.05 mg/kg) was injected subcutaneously right after the procedure. The animals were kept on top of a warming pack until recovery from anesthesia. D-TZP or TZP (10 mg/kg PMB equivalent) was administered by IV injection at 2 h post-CLP and every subsequent 2 days a maximum total of three times (CLP+2 h→treatment, IV, q2d×3). A vehicle control (5% dextrose) or 5 mg/kg (IV $LD_{50}$) free PMB was administered in the same manner. Animals were monitored as described in the endotoxemia model.

Cytokine and D-dimer levels in CLP. CLP procedure was performed on 6 week-old C57BL/6 male mice, and D-TZP or TZP (10 mg/kg PMB eq.) was administered by IV at 2 h post-CLP. Five percent dextrose was administered as a vehicle control. Three hours (for cytokine measurement) or 24 h (for D-dimer) after CLP, blood was obtained by cardiac puncture and collected in a BD Vacutainer tube (lithium heparin). Plasma was separated from blood through 10 min centrifugation at 1,000 rcf and diluted with assay diluents, 5 times for TNF-α, 20 times for IL-10, and 10 times for D-dimer analysis. TNF-α, IL-10, and D-dimer in the diluted plasma were quantified by the enzyme-linked immunosorbent assay (ELISA). The absorbance was measured at 450 nm by a Spectra Max M3 microplate reader.

Pharmacokinetics/Biodistribution of PMB. 6-8 week-old C57BL/6 male mice were administered with free PMB or D-TZP at a dose equivalent to PMB 5 mg/kg by tail vein injection. At predetermined time points, 3 mice per group were sacrificed for the collection of blood and major organs. Blood was obtained by cardiac puncture and collected in a BD Vacutainer tube (lithium heparin). The blood was divided to two parts. One of them was analyzed as is (whole blood), and the other was centrifuged at 1,000 rcf for 10 min to obtain plasma. Atlantis T3 column (15 cm×2.1 mm, particle size: 3 μm) was used for the analysis.

Blood in SEM. 6 week-old C57BL/6 male mice were administered with 10 mg/kg eq. D-TZP. After 30 min, blood was obtained by cardiac puncture and collected in a BD Vacutainer tube (lithium heparin). Blood cells were separated from the plasma by 10 min centrifugation at 1,000 rcf, rinsed with PBS, and resuspended in 1 mL of PBS. Twenty five microliters of the cell suspension was mixed with 475 μL of PBS, followed by the addition of 500 μL 2.5% glutaraldehyde solution. After 30 min incubation in the dark, 200 μL of the fixed cell suspension was placed on a poly-1-lysine-coated coverslip. After 1 h, the coverslip was rinsed three times with water (5 min each) and incubated in 2% Osmium tetroxide for 1 h. SEM imaging was performed as described in previous section.

Statistical analysis. Statistical analysis of all data was performed by the GraphPad Prism 8 (La Jolla, CA). One-way ANOVA was used to determine the statistical difference among different groups, followed by the recommended multiple comparisons test. A p-value of <0.05 was considered statistically significant.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES

1. Gotts, J. E.; Matthay, M. A., Sepsis: pathophysiology and clinical management. *BMJ* 2016, 353, i1585.
2. Rudd, K. E. et al. Global, regional, and national sepsis incidence and mortality, 1990-2017: analysis for the Global Burden of Disease Study. *The Lancet* 395, 200-211 (2020).
3. van der Poll, T., van de Veerdonk, F. L., Scicluna, B. P. & Netea, M. G. The immunopathology of sepsis and potential therapeutic targets. *Nature Reviews Immunology* 17, 407 (2017).

4 Beutler, B. & Rietschel, E. T. Innate immune sensing and its roots: the story of endotoxin. *Nature Reviews Immunology* 3, 169-176 (2003).

5 Rittirsch, D., Flierl, M. A. & Ward, P. A. Harmful molecular mechanisms in sepsis. *Nature Reviews Immunology* 8, 776-787 (2008).

6 Cavaillon, J.-M., Singer, M. & Skirecki, T. Sepsis therapies: learning from 30 years of failure of translational research to propose new leads. *EMBO Mol Med* 12, e10128 (2020).

7 Howell, M. D. & Davis, A. M. Management of Sepsis and Septic Shock. *JAMA* 317, 847-848 (2017).

8 Fink, M. P. & Warren, H. S. Strategies to improve drug development for sepsis. *Nature Reviews Drug Discovery* 13, 741 (2014).

9 Ranieri, V. M. et al. Drotrecogin Alfa (Activated) in Adults with Septic Shock. *The New England Journal of Medicine* 366, 2055-2064 (2012).

10 Sprung, C. L. et al. Hydrocortisone Therapy for Patients with Septic Shock. *N Engl J Med* 358, 111-124 (2008).

11 Opal, S. M. et al. Effect of Eritoran, an Antagonist of MD2-TLR4, on Mortality in Patients With Severe Sepsis: The ACCESS Randomized Trial *JAMA* 309, 1154-1162 (2013).

12 López, A. et al. Multiple-center, randomized, placebo-controlled, double-blind study of the nitric oxide synthase inhibitor 546C88: Effect on survival in patients with septic shock*. 32, 21-30 (2004).

13 Reinhart, K. et al. Assessment of the safety and efficacy of the monoclonal anti-tumor necrosis factor antibody-fragment, MAK 195F, in patients with sepsis and septic shock: A multicenter, randomized, placebo-controlled, dose-ranging study. 24, 733-742 (1996).

14 Dellinger, R., Bagshaw, S. M., Antonelli, M. & et al. Effect of targeted polymyxin b hemoperfusion on 28-day mortality in patients with septic shock and elevated endotoxin level: The euphrates randomized clinical trial. *JAMA* 320, 1455-1463 (2018).

15 McCloskey, R. V., Straube, R. C., Sanders, C., Smith, S. M. & Smith, C. R. Treatment of septic shock with human monoclonal antibody HA-1A. A randomized, double-blind, placebo-controlled trial. CHESS Trial Study Group. *Annals of internal medicine* 121, 1-5 (1994).

16 Marshall, J. C. Why have clinical trials in sepsis failed? *Trends in Molecular Medicine* 20, 195-203 (2014).

17 Buras, J. A., Holzmann, B. & Sitkovsky, M. Animal models of sepsis: Setting the stage. *Nature Reviews Drug Discovery* 4, 854-865 (2005).

18 Clinical and Laboratory Standards Institute, C. *Methods for Dilution Antimicrobial Susceptibility Tests for Bacteria That Grow Aerobically; Approved Standard—Ninth Edition* (Clinical and Laboratory Standards Institute, 2012).

19 Copeland, S., Warren, H. S., Lowry, S. F., Calvano, S. E. & Remick, D. Acute Inflammatory Response to Endotoxin in Mice and Humans. *Clinical and Diagnostic Laboratory Immunology* 12, 60 (2005).

We claim:

1. A process for preparing a pharmaceutical composition of zwitterionic chitosan (ZWC) coated-tannic acid-Fe (TZ) nanoparticles (NPs) comprising the step of:
   a. adding an ethanol solution of tannic acid to an aqueous solution of $FeCl_3$ to afford tannic acid-Fe (T) nanoparticles (NPs);
   b. preparing succinylated chitosan to afford zwitterionic chitosan (ZWC);
   c. adding ZWC to said T NPs to afford ZWC-coated tannic acid-Fe NPs (ZWC-T NPs, or TZ); and
   d. adding one or more active pharmaceutical ingredients at an elevated pH to above prepared TZ to afford a stable form of zwitterionic chitosan-coated tannic acid-Fe nanoparticles (TZ).

2. The process of claim 1, wherein said ethanol solution of tannic acid further comprises a component of vitamin $D_3$.

3. The process of claim 1, wherein said active pharmaceutical ingredient is a positively charged therapeutic compound.

4. The process of claim 3, wherein said positively charged therapeutic compound is polymyxin B (PMB), polyethyleneimine, cathelicidin, colistin (aka polymyxin E), or an apolipoprotein.

5. The process of claim 3, wherein said positively charged therapeutic compound is polymyxin B (PMB).

6. A pharmaceutical composition comprising the zwitterionic chitosan (ZWC) coated-tannic acid-Fe (TZ) nanoparticles (NPs) manufactured according to claim 1, wherein said pharmaceutical composition further comprises one or more diluents, excipients or carriers.

7. The pharmaceutical composition of claim 6, wherein said active pharmaceutical ingredient added to make said zwitterionic chitosan (ZWC) coated-tannic acid-Fe (TZ) nanoparticles (NPs) is a positively charged therapeutic compound.

8. A method for treating a patient with sepsis comprising administering to said patient a therapeutically effective amount of the pharmaceutical composition of claim 6.

9. The pharmaceutical composition of claim 7, wherein said positively charged therapeutic compound is polymyxin B, polyethyleneimine, cathelicidin, colistin (polymyxin E), or an apolipoprotein.

10. The pharmaceutical composition of claim 7, wherein said positively charged therapeutic compound is polymyxin B (PMB).

11. The pharmaceutical composition of claim 6, wherein said ethanol solution of tannic acid added to make said zwitterionic chitosan (ZWC) coated-tannic acid-Fe (TZ) nanoparticles (NPs) comprises a component of vitamin $D_3$.

12. A method of treating a patient with a disease comprising administering to the patient a therapeutically effective amount of the pharmaceutical composition of claim 6.

13. The method of claim 12, wherein said disease is sepsis.

* * * * *